(12) United States Patent
Helfenbein et al.

(10) Patent No.: US 6,227,854 B1
(45) Date of Patent: May 8, 2001

(54) RELEASABLE CHUCKING DEVICE FOR A ROTATING MEDICAL OR DENTAL TOOL

(75) Inventors: Gerald Helfenbein, Moosdorf; Norbert Schatz, Bürmoos, both of (AT)

(73) Assignee: Dentalwerk Bürmoos Gesellschaft m.b.H., Bürmoos (AT)

( * ) Notice: Subject to any disclaimer, the term of this patent is extended or adjusted under 35 U.S.C. 154(b) by 0 days.

(21) Appl. No.: 09/315,687

(22) Filed: May 20, 1999

(30) Foreign Application Priority Data

May 20, 1998 (AT) ....................................... 872/98

(51) Int. Cl.[7] ....................................... A61C 1/14
(52) U.S. Cl. ............................... 433/128; 433/127
(58) Field of Search ...................... 433/127, 128, 433/129; 279/46.3, 46.7, 50

(56) References Cited

U.S. PATENT DOCUMENTS

| | | | |
|---|---|---|---|
| 2,911,721 | * | 11/1959 | Staunt . |
| 4,398,886 | * | 8/1983 | Schuss et al. .................. 433/128 |
| 4,661,062 | * | 4/1987 | Seigneurin ..................... 433/128 |
| 5,011,408 | * | 4/1991 | Nakanishi ...................... 433/127 |
| 5,037,299 | * | 8/1991 | Nakanishi ...................... 433/128 |
| 5,090,906 | * | 2/1992 | Pernot .......................... 433/127 |
| 5,591,028 | * | 1/1997 | Fujiki et al. ................... 433/129 |
| 5,653,453 | * | 8/1997 | Nakamoto ........................ 279/50 |
| 5,730,596 | * | 3/1998 | Rosenstatter ................... 433/127 |
| 5,836,766 | * | 11/1998 | Gugel et al. ................... 433/127 |

FOREIGN PATENT DOCUMENTS

| | | |
|---|---|---|
| 3012240 | 10/1981 | (DE) . |
| 3442386 | 6/1985 | (DE) . |
| 8913626 | 5/1991 | (DE) . |
| 0470324 | 2/1992 | (EP) . |
| 0322896 | 3/1993 | (EP) . |
| 0820734 | 1/1998 | (EP) . |

* cited by examiner

Primary Examiner—Ralph A. Lewis
(74) Attorney, Agent, or Firm—Friedrich Kueffner

(57) ABSTRACT

A releasable chucking device for a rotating medical or dental tool includes a tool shaft with a chucking end, wherein the chucking end of the tool shaft has a flattened portion and an annular groove in the area of the flattened portion, wherein the chucking device further includes a holding member protruding radially inwardly into the annular groove during operation, and an additional frictionally engaging support of the tool, for example, by providing the sleeve surrounding the circular cylindrical portion of the tool shaft with a collet or to construct the sleeve as a collet.

9 Claims, 6 Drawing Sheets

RELEASABLE CHUCKING DEVICE FOR A ROTATING MEDICAL OR DENTAL TOOL

BACKGROUND OF THE INVENTION

1. Field of the Invention

The present invention relates to a releasable chucking device for a rotating medical or dental tool.

2. Description of the Related Art

A special type of medical or dental tools, which are operated with relatively high torques, have at the chucking end in the tool shaft a flattened portion for transmitting the torque. In addition, the tools have in the area of the flattened portion an annular groove, wherein a holding member of the chucking device protrudes radially inwardly into the annular groove during the operation of the tool in order to hold the tool in axial direction.

The circular cylindrical tool shaft is received in a circular cylindrical recess of the handpiece head with as little play as possible. This play usually is a few hundredth of a millimeter in the radial direction; this is due to the tolerances of the dimensions particularly of the tool shafts.

However, in a chucking device of the above-described type, even this little play has drastic effects on the operation of such tools because of the extremely small dimensions of the tool and, thus, of the tool head. This is because a play of a few hundredth of a millimeter means that the drill is movable in an order of magnitude which may correspond to half the chucking height. Particularly in view of the rates of rotation used in such tools, this means that the dimensional accuracy of the bore is significantly impaired, the quality of the bore surface and the bore edges is significantly reduced and vibrations and pain for the patient are increased.

Tool holders for such tool shafts are known, for example, from DE 30 12 240 A, DE 34 42 386 A, DE-G 89 13 626.8 U, EP 0 322 896 B, EP 0 470 324 B, and EP 0 820 734 A. All these known tool holders have the disadvantages described above.

SUMMARY OF THE INVENTION

Therefore, it is the primary object of the present invention to provide a tool chucking device in which the above-described disadvantages do not occur and which still has all the advantages of the previously known tool holders.

In accordance with the present invention, this object is met by providing an additional frictionally engaging support of the tool, for example, by providing the sleeve surrounding the circular cylindrical portion of the tool shaft with a collet or to construct the sleeve as a collet.

As a result of the configuration according to the present invention, an additional frictionally engaging support of the tool shaft is achieved, wherein the support is free of play and the holding force is certainly sufficient for the fixed support during the usual operation, aside from the forces necessary for transmitting the drive torque, and produces during normal operation an essentially play-free support, which, in addition, centers the tool.

In accordance with a further development of the invention, the collet is released by actuating a push button, wherein this push button also releases the radial engagement in the area of the groove of the tool shaft.

The present invention also relates to a special configuration of this radially releasable engagement.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

Figure 1:
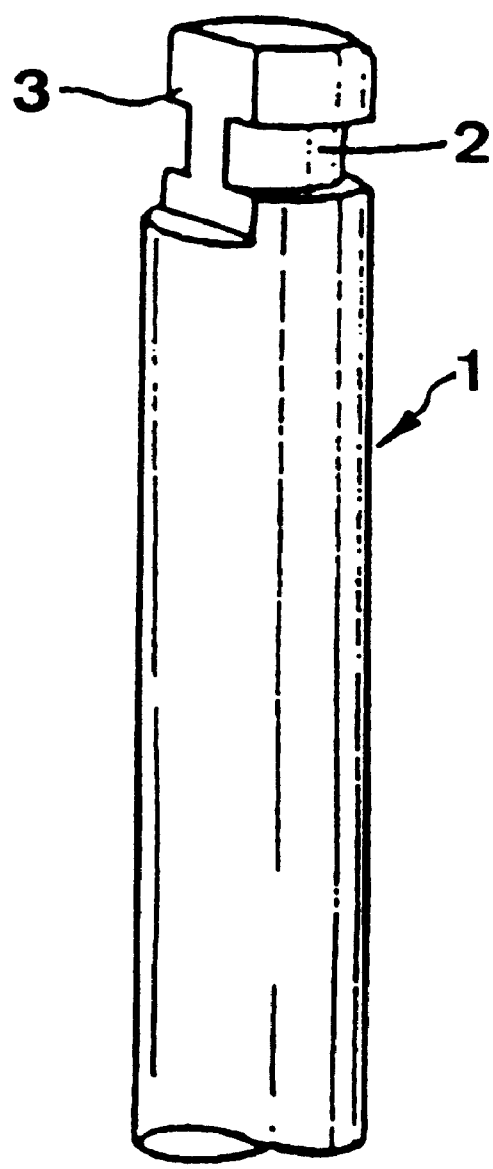
FIG. 1 is a partial perspective view of a tool shaft which is to be supported by the chucking tool according to the present invention.

FIG. 1 of the drawing shows the end of a tool shaft 1 on the side of the handpiece. This tool shaft 1 has an annular groove 2 and a flattened portion 3. Tool shafts of this type are standardized and have been known for a long time and serve particularly for transmitting high torques. This transmission of the torque is effected by means of a projection provided in and rotating with the tool holder, wherein the projection interacts in a positively engaging manner with the flattened portion 3. The annular groove 2 serves to axially secure the tool because, in accordance with the prior art, this tool is inserted into a tool receiving element with as little play as possible but otherwise not supported, so that the tool is not fixedly secured in the axial direction.

Figure 2:
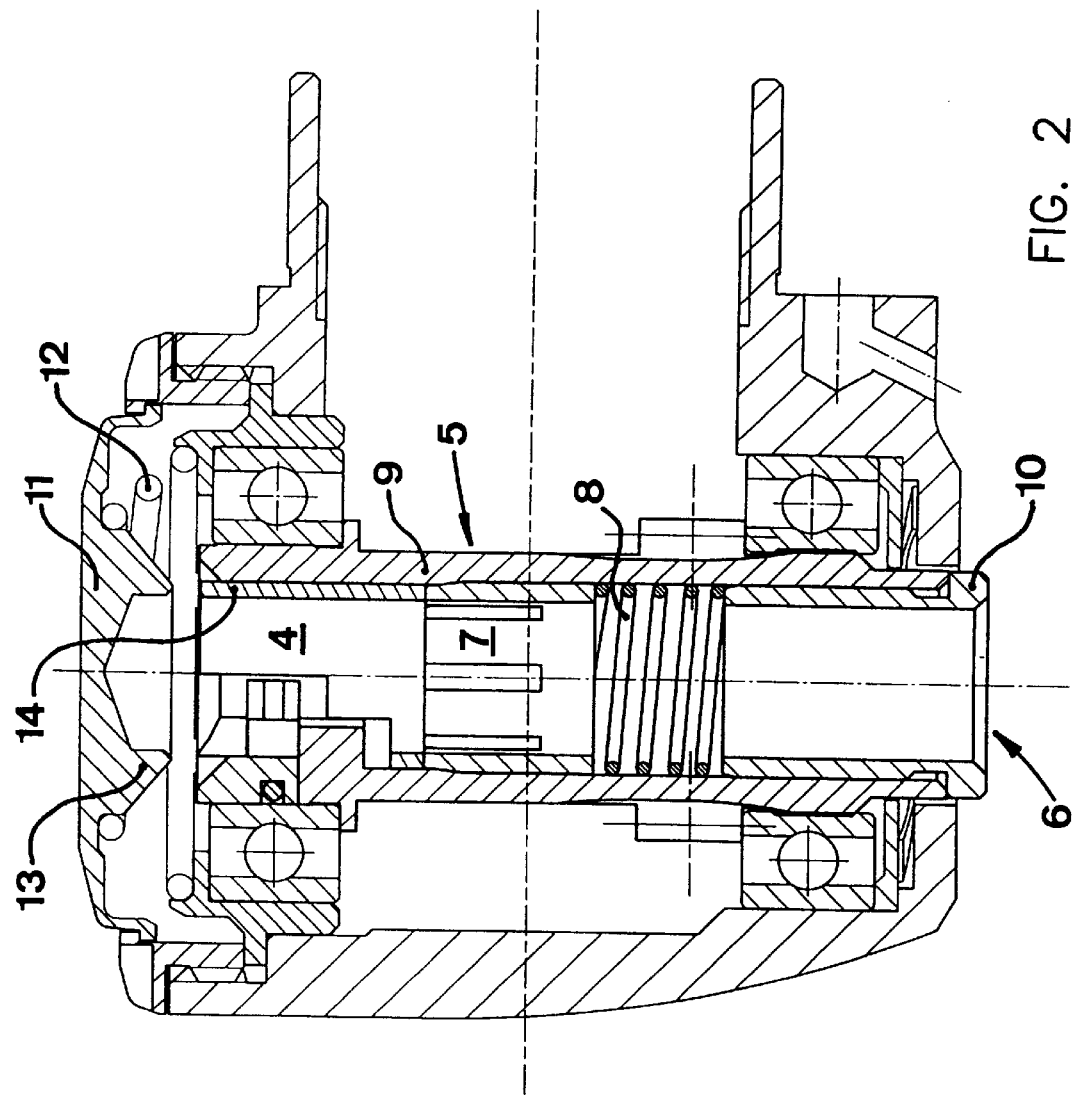
FIG. 2 is a sectional view, on a larger scale, of the head of a dental angle piece with the collet according to the present invention.

FIG. 2 shows a tool holder 4 according to the present invention. This tool is provided in its upper portion with the conventional elements for receiving such tools; these elements will be described in more detail below in connection with a specific embodiment of the invention.

The tool holder 6 is constructed in the middle portion 5 thereof as a collet 7 which is forced by a spring 8 into the closed position for holding the tool. For this purpose, the collet 7 is constructed at its upper end with a conical outer surface and interacts with a corresponding conical surface of an outer sleeve 9. The spring 8 rests with one end thereof against the collet 7 and with its other end against a press-in sleeve 10 which is fixedly mounted in the outer sleeve 9.

The collet 7 is actuated by a push button 11 which can be pressed downwardly, for example, by the thumb of the user against the force of a spring 12. During this movement, an annular projection 13 of the push button 11 is moved into the area of a push sleeve 14 which is seated in an aligned manner on the individual resilient ends of the collet 7. At its end facing the push button 11, the push sleeve 14 has a recess to permit the engagement and movement of the conventional holding mechanism for the flattened portion and the annular groove of the tool shaft.

At its end facing the collet, the sleeve 14 is of continuous construction in the circumferential direction and, thus, transmits the pressure applied to the push button 11 essentially concentrically to the collet 7.

Figure 3:
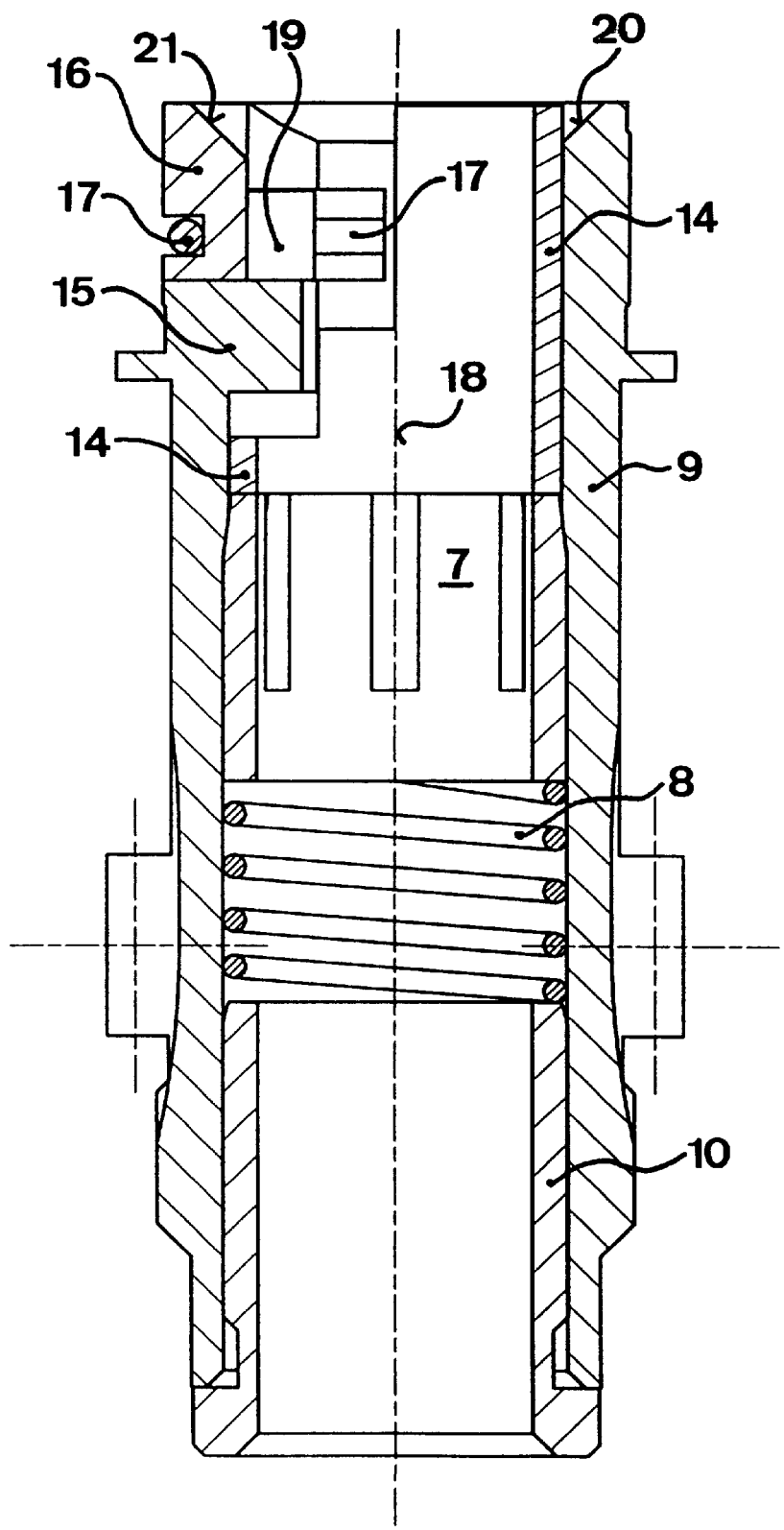
FIG. 3 is a sectional view, on an even larger scale, showing the actual chucking device of FIG. 2.

The chucking device is illustrated in FIG. 3 on a larger scale and in more detail.

The outer sleeve 9 is provided with a projection 15 which interacts with the flattened portion 3 of the tool shaft 1 and limits the depth by which the tool can be inserted. The projection 15 is of such solid construction that it at least substantially compensates the imbalance which is unavoidable as a result of the shape of the tool shaft. In the illustrated preferred embodiment, the axial support is effected by an element 16 which is essentially half ring-shaped or horseshoe-shaped and is placed in a corresponding recess of the outer sleeve 9 and is held in the outer sleeve 9 by a curved spring 17 and is pressed toward the axis 18 of the tool holder.

The axial support 16 has two lateral projections 19, wherein FIG. 3 only shows the projection 19 located behind the sectional plane. These two projections 19 are forced by the force of the spring 17 into the groove 2 of the tool shaft 1.

FIG. 3 shows the recesses in the push sleeve 14 and the outer sleeve 9 in the areas of the two projections 19 through which the spring 17 can be seen.

The outer sleeve 9 is provided at its upper inner edge with a bevel 20 which serves as a locking means and as a means for limiting the movement of the push button 11 seen in FIG. 2. The axial securing means 16 also is provided with a similar bevel 21. The movement of the push button 11 forces the axial securing means 16 outwardly and to the left as seen in FIGS. 2 and 3. This movement also presses the push sleeve 14 downwardly against the force of the spring 8, so that the collet 7 is released in the area of the internal conical surface of the outer sleeve 9 and opens outwardly as a result of the elasticity of the individual elements of the collet.

Figure 4:
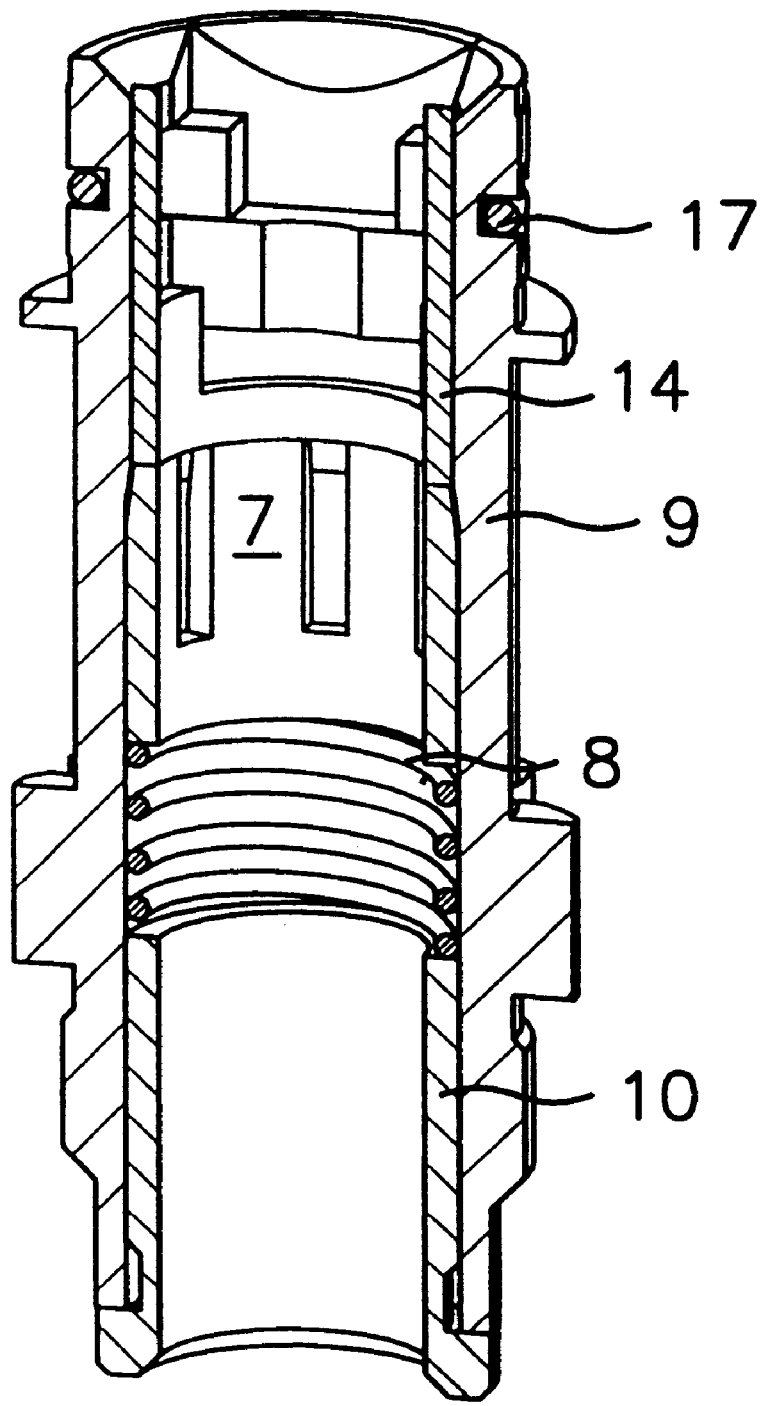
FIGS. 4 and 5 are isometrical views of the tool chucking device according to the present invention cut open in the axial direction and seen from different angles of view.
Figure 5:
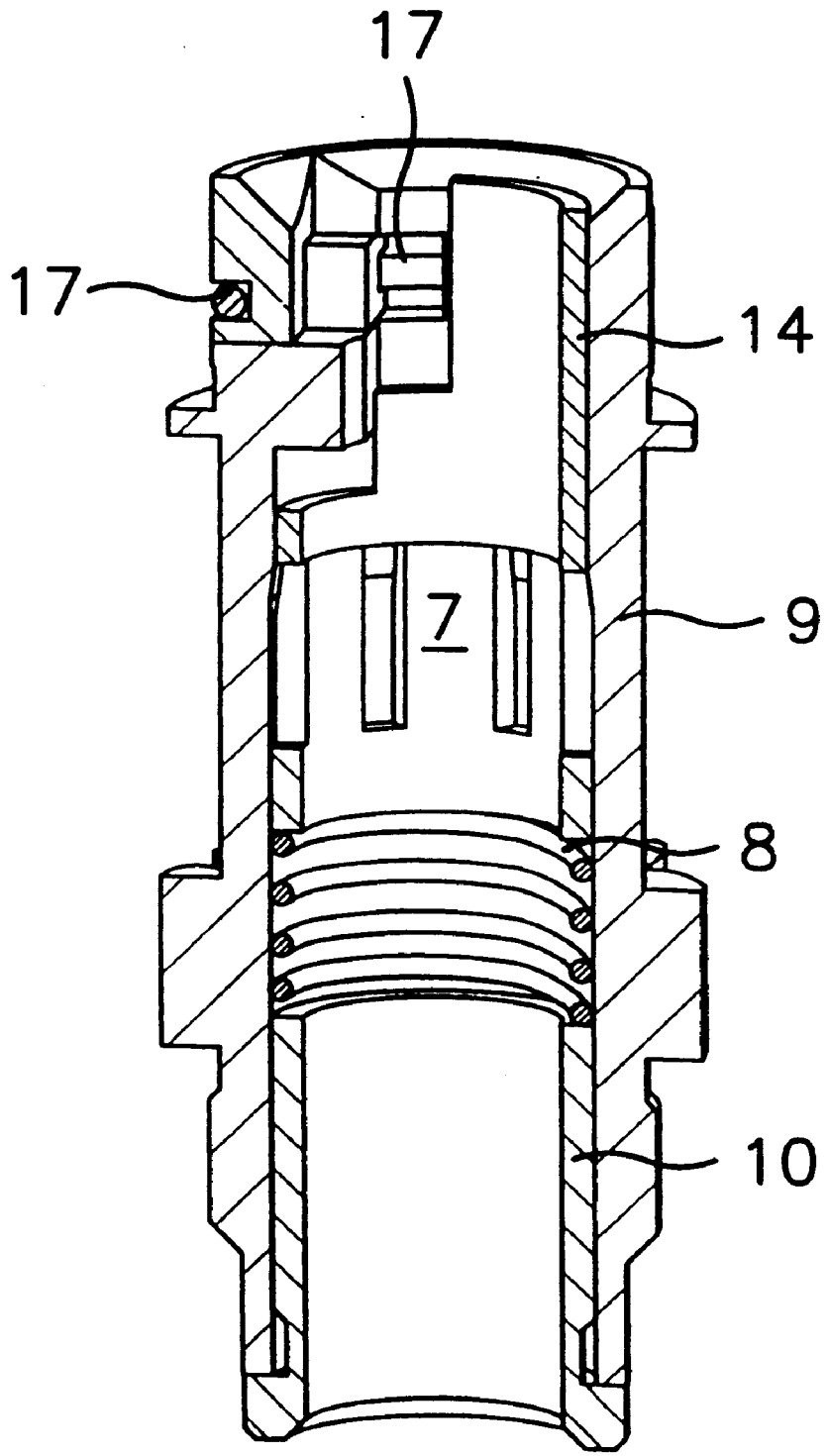

For illustrating the construction of the chucking device according to the present invention, FIGS. 4 and 5 show from two different directions a tool holder cut open in axial direction.

Figure 6:
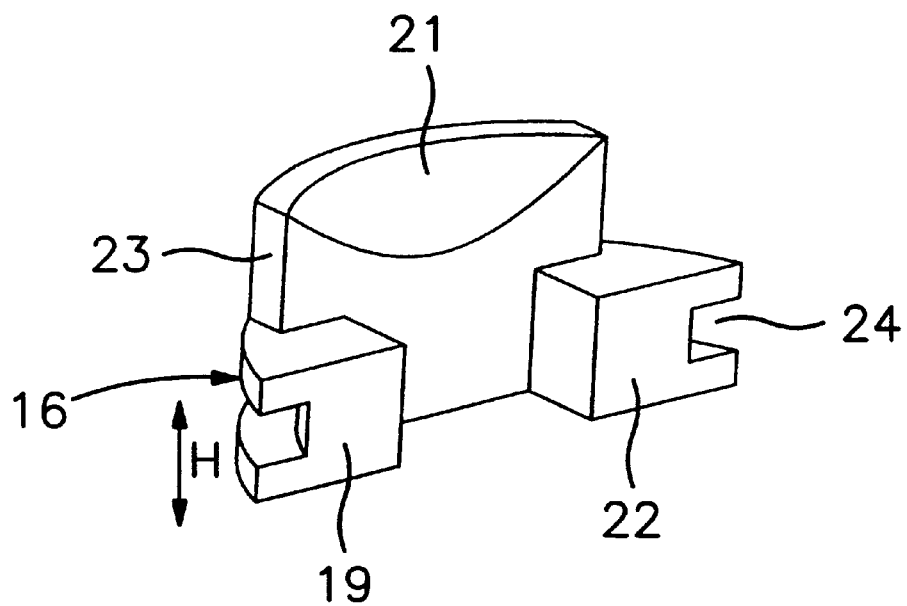
FIG. 6 is a perspective view showing a detail of the chucking device according to the present invention.

FIG. 6 shows an axial support means 16 according to the present invention. The axial support means 16 is composed of an essentially circular segment-shaped cylindrical portion 22 whose height H is smaller than or equal to the height of the annular groove 2 of the tool shaft 1, and a wall portion 23 adjacent the cylindrical portion 22, wherein the wall portion 23 has at its end facing away from the cylindrical portion 22 a bevel 21.

In the active state of the tool holder, the inner side of the wall portion 23 rests against the flattened portion 3 of the tool shaft 1, wherein the parts of the cylindrical portion 22 which form projections 19 and protrude beyond the wall portion engage in the annular groove 2 of the tool shaft 1 and cause the tool shaft to be secured axially. In accordance with another embodiment not shown in the drawing, the height of the projections 19 may be constructed so as to decrease in an inner portion starting at the wall portion 23 in order to compensate the tolerances in the annular groove 2 of the tool shaft 1 which always are present. In that case, it is advantageous if the collet only exerts a significant holding force when the projections 19 are already fully engaged in the annular groove 2.

The axial holder 16 according to the present invention can also be used in tool holders which do not have a frictionally engaging support of the tool; this results in a better mass distribution of the rotating masses and, due to the wall portion pressed against the tool shaft, in a better support than was possible in previously known tool holders.

The present invention is not limited to the illustrated embodiments; rather, various modifications are possible. For example, especially the collet may be constructed differently from the one illustrated in the drawing. Thus, for example, the clamping elements of the collet may face in the direction of the end of the tool, or it may be constructed as a double collet. Analogous to these embodiments, the conical surfaces may also be constructed differently and may be arranged on different components. Finally, the collet may be in the form of a type of helical spring which, when an axial pressure is exerted, increases its diameter to such an extent that it releases the tool shaft.

Other embodiments concern, for example, the axial holder 16 which, contrary to the illustrated embodiment, may have a configuration disclosed in one of the references listed above. It is even possible to omit the axial holder because, when the spring 8 and the internal conical surface of the outer sleeve 9 are dimensioned appropriately, the holding force of the collet according to the present invention may be sufficient for securing the tool even when the tool is used for working with an outwardly pulling operation. However, for reasons of safety, this embodiment is not preferred.

While specific embodiments of the invention have been shown and described in detail to illustrate the inventive principles, it will be understood that the invention may be embodied otherwise without departing from such principles.

What is claimed is:

1. A releasable chucking device for a rotating medical or dental tool having a tool shaft with a chucking end, wherein the chucking end of the tool shaft has a flattened portion and an annular groove in the area of the flattened portion, the chucking device comprising:

a tool holder having an outer sleeve configured to receive the tool shaft, a releasable holding member arranged in the outer sleeve and protruding radially inwardly into the annular groove during operation, a frictionally engaging support arranged axially adjacent to the holding member in the outer sleeve and configured to frictionally engage a circular cylindrical portion of the tool shaft.

2. The chucking device according to claim 1, wherein the frictionally engaging support is a collet.

3. The chucking device according to claim 2, further comprising a push button arranged on an end of the outer sleeve for actuating the collet, wherein the end of the outer sleeve has a push sleeve, wherein the collet comprises resilient elements configured to frictionally engage the circular cylindrical portion, wherein the push button comprises a push button spring forcing the push button into a rest position away from the push sleeve, wherein the push button is configured to act, when actuated, via the push sleeve against a force of the push button spring onto the resilient elements of the collet to release the resilient elements from the circular cylindrical portion.

4. The chucking device according to claim 3, wherein the push button has an annular projection, wherein the holding member has a bevel facing the annular projection and a holding member spring forcing the holding member radially inwardly, wherein the annular projection exerts a radially outwardly directed force against the bevel of the holding member when the push button is actuated, and wherein the axially directed force moves the holding member radially outwardly against a force of the holding member spring.

5. The chucking device according to claim 4, wherein the annular projection is configured to press against the push sleeve.

6. The chucking device according to claim 4, wherein the holding member is comprised of a circular segment-shaped cylindrical portion having a height which is smaller than or equal to a height of the annular groove of the tool shaft, and a wall portion adjacent to the cylindrical portion, wherein the wall portion is provided with the bevel at the end facing away from the cylindrical portion.

7. The chucking device according to claim 6, wherein the cylindrical portion has an annular groove for receiving the holding member spring.

8. The chucking device according to claim 7, wherein the holding member spring is a curved spring.

9. The chucking device according to claim 6, wherein the cylindrical portion has projections projecting relative to the wall portion radially inwardly and having a height relative to the wall portion which decreases starting from the wall portion at least in a radially inner area thereof.

* * * * *